United States Patent
Bunz

(10) Patent No.: US 6,802,866 B2
(45) Date of Patent: Oct. 12, 2004

(54) HIP JOINT PROSTHESIS WITH ABUTMENT-PROTECTED PROSTHESIS SHAFT

(75) Inventor: Uwe Bunz, Wolfschlugen (DE)

(73) Assignee: CeramTec AG Innovative Ceramic Engineering, Plochingen (DE)

(*) Notice: Subject to any disclaimer, the term of this patent is extended or adjusted under 35 U.S.C. 154(b) by 0 days.

(21) Appl. No.: 10/242,283

(22) Filed: Sep. 12, 2002

(65) Prior Publication Data

US 2003/0055510 A1 Mar. 20, 2003

(30) Foreign Application Priority Data

Sep. 19, 2001 (DE) .......................... 101 46 075
Apr. 27, 2002 (DE) .......................... 102 18 978

(51) Int. Cl.⁷ ............................................. A61F 2/32
(52) U.S. Cl. .............................. 623/22.14; 623/22.15
(58) Field of Search .................... 623/17.11, 17.14, 623/19.11, 19.12, 20.21, 20.22, 20.25, 20.26, 21.15, 21.16, 22.11, 22.13, 22.14, 22.4, 22.43, 22.44, 22.45, 22.46, 23.5, 23.11, 23.12, 23.13, 23.14, 23.15

(56) References Cited

U.S. PATENT DOCUMENTS

| | | | | |
|---|---|---|---|---|
| 4,032,994 A | * | 7/1977 | Frey ............................ 3/1.912 |
| 4,538,305 A | * | 9/1985 | Engelbrecht et al. ......... 623/20 |
| 4,687,488 A | * | 8/1987 | Frey ............................ 623/22 |
| 4,908,034 A | * | 3/1990 | Weightman et al. .......... 623/23 |
| 5,015,257 A | * | 5/1991 | Crowninshield et al. ...... 623/22 |
| 5,037,441 A | * | 8/1991 | Bouvet ........................ 623/23 |
| 5,156,624 A | * | 10/1992 | Barnes ........................ 623/22 |
| 5,362,311 A | * | 11/1994 | Amino et al. ................. 623/22 |
| 5,405,394 A | * | 4/1995 | Davidson ..................... 623/18 |
| 5,735,905 A | * | 4/1998 | Parr ............................ 623/23 |
| 6,096,083 A | * | 8/2000 | Keller et al. ............. 623/22.11 |
| 6,607,560 B1 | * | 8/2003 | Pfaff et al. ............... 623/22.45 |
| 2002/0116068 A1 | * | 8/2002 | McLean .................. 623/22.15 |

FOREIGN PATENT DOCUMENTS

FR 2254239 * 7/1975 ........... F16C/27/06

* cited by examiner

Primary Examiner—Kevin Shaver
Assistant Examiner—Anuradha Ramana
(74) Attorney, Agent, or Firm—Fulbright & Jaworski L.L.P.

(57) ABSTRACT

A hip joint prosthesis has an external metal shell, an internal socket insert in which a ball head can rotate. The ball head is joined to a metal prosthesis shaft of the femoral shaft component and the movement of the prosthesis shaft is limited by abutting against the margin of the socket insert. A soft, biocompatible cushioning element is applied to the socket insert on the circumferential surface of the prosthesis shaft.

12 Claims, 4 Drawing Sheets

HIP JOINT PROSTHESIS WITH ABUTMENT-PROTECTED PROSTHESIS SHAFT

BACKGROUND AND SUMMARY OF THE INVENTION

The invention relates to a hip joint prosthesis with an outer metal shell, an inner socket insert in which a ball head articulates, the ball head is joined to a metal prosthesis shaft of the femoral shaft component, and the movement of the prosthesis shaft is limited by abutting against the margin of the socket insert.

In today's prostheses the movement of the femoral shaft component is limited by measures taken on the hip joint socket. There are various embodiments, e.g.:

A raised metal edge

A raised PE edge (PE=polyethylene) in sandwich systems (e.g., U.S. Pat. No. 5,879,404)

The PE, ceramic or metal insert itself.

In this case the prosthesis shaft is mostly not optimally matched to its counterpart. In shaft prostheses, three positions of the prosthesis shaft with respect to the hip joint socket are often possible.

These said structural designs results in various disadvantages:

Optimization of the shaft component in regard to abutment cannot be achieved. Therefore no adaptation of the abutment geometry to minimize the surface pressure is possible. Furthermore, any adaptation of the shaft component to all possible installation positions is likewise impossible.

When the metal shaft abuts against a metal or ceramic insert, metal detritus is released which can lead to the known negative effects.

In the case of abutment against PE, flow of the PE cannot be avoided. The implant becomes unstable and severe PE deformation can lead to situations wherein the functionality of the implants is not assured.

The PE in the hip joint socket is not optimized for cushioning shaft abutment, since its material and shape are optimized for use as parts in frictional contact with one another. Above all, no defined cushioning of the abutment is possible. In the event of elevated impulse energies this can result in the failure of an implant.

The invention is addressed to the problem of improving a hip joint prosthesis according to the preamble of claim 1 with respect to the abutment of the prosthesis shaft against the socket insert.

This problem is solved by the invention in that a soft, biocompatible cushioning element is applied to the circumferential surface of the prosthesis shaft where the latter impacts the socket insert.

In a preferred embodiment the cushioning element is made from a plastic, e.g., PE (polyethylene), PEI (polyether imide), silicone or TPE (thermoplastic elastomer), to name but a few.

Advantageously, the geometric configuration of the cushioning element is matched to the corresponding edge of the socket insert, i.e., the edge of the socket insert can engage the cushioning element upon abutment, or vice versa.

For this purpose recesses for the corresponding edge of the socket insert are made preferably in the cushioning element's surface confronting the socket insert. These indentations form a replica of the edge of the socket insert.

It may be advantageous if the axial length of the cushioning element reaches all the way into the ball head. In this way extremely good fixation can be achieved.

In a preferred embodiment, the cushioning element is a ring, advantageously a ring with a slot which can be, for example, axial, at an angle, and/or in a sawtooth manner. The slot makes possible easy assembly of the cushioning element on the prosthesis shaft.

The ends of the slot are advantageously out of line with one another so that cushioning is always achieved wherever abutment occurs.

In a preferred embodiment, cavities are arranged between the cushioning element and the prosthesis shaft to contain body fluids. When the prosthesis shaft strikes the socket insert these cavities are compressed and the body fluid is driven out, so that cushioning is the result.

The idea of the present invention is to apply to the prosthesis shaft a biocompatible layer that is soft in comparison to the metal shaft. The geometrical configuration of this layer is adapted to the corresponding hip joint socket in order to minimize the surface pressures occurring in case of abutment. The structural configuration of the hip joint socket can include a directly clamped design, a sandwich design, a press fit system or a screw-in socket system. The material of this interlayer is preferably a plastic (PE, PEI, silicone, TPE, . . . )

The following are the advantages of this invention over the state of the art:

The system permits optimization as regards an enlarged range of movement (ROM). Abutment optimization has been performed heretofore either on the prosthesis shaft or on the hip joint socket. These defined abutments have been in some cases (raised metal margin) obtained with a limitation of the ROM. By consideration of the overall system and coordination as regards abutment, openings or recesses can be created in the soft biocompatible layer, to increase the ROM.

Optimization of the "abutment" state of operation is possible: This includes adaptation of the abutment geometry of the soft biocompatible layer to minimize the surface pressure that is present and an adaptation of the shaft component to all possible installed positions. These installed positions are defined by different lengths of the neck of the ball heads.

In the event of abutment of the shaft it is possible by appropriate selection of the material of the soft biocompatible layer to assure that very little biocompatible material is released (no metal detritus/no PE flow).

A defined cushioning of the abutment is possible:

By the use of materials with high internal damping qualities and by the functional separation of the bodies in friction and the cushioning element, both internal damping and structural damping elements are possible. Cushioning is achieved in excess of the level of the internal damping by a controlled escape of body fluids (substantially water).

Additional features of the invention will be found in the figures which are described below.

BRIEF DESCRIPTION OF THE DRAWINGS

FIG. 10b show a section along line A—A in FIG. 10a.

DETAILED DESCRIPTION

Figure 1:
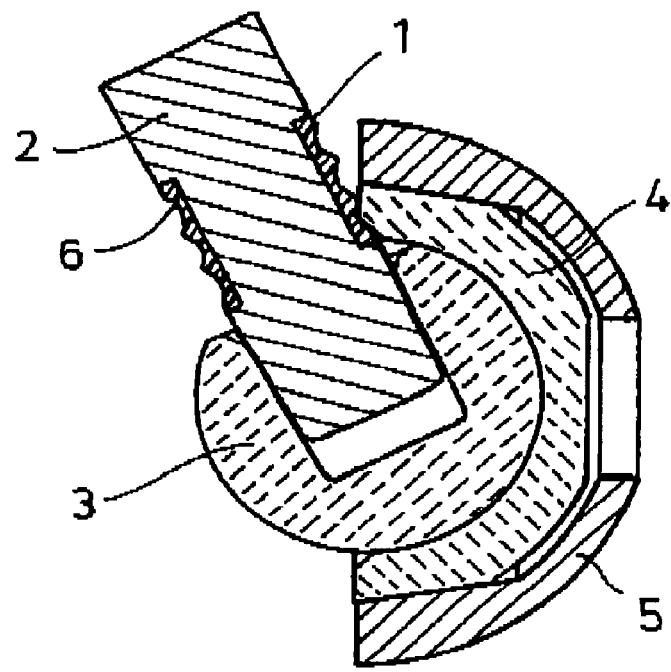
FIG. 1 is a cross section of an embodiment of a hip joint prosthesis according to the present invention.

A ceramic socket insert 4 is placed in an outer metal shell 5. At the lower end an opening is arranged in the metal shell 5.

In the socket insert 4 a ceramic ball head 3 articulates, which is joined to a metal prosthesis shaft 2 of the femoral shaft component. For this purpose the prosthesis shaft 2 is usually anchored in the ball head 3 by a tapered friction joint in a tapered bore.

The movement of the prosthesis shaft 2 is limited by abutting on the edge of the socket insert 4. In the area of the abutment a soft, biocompatible cushioning element 1 is installed. In the embodiment here shown, this cushioning element is in the form of a ring placed on the prosthesis shaft. The ring consists of a plastic, such as polyethylene (PE), PEI, silicone or TPE.

A groove is provided in the prosthesis shaft 2, in which the ring or cushioning element 1 is installed.

The geometric configuration of the cushioning element 1 is adapted to the corresponding edge of the socket insert 4 by means of indentations 6. These indentations 6 are shaped so that the edge of the socket insert 4 can enter into them. Thus the maximum freedom of movement of the prosthesis shaft 2 is increased.

Figure 2:
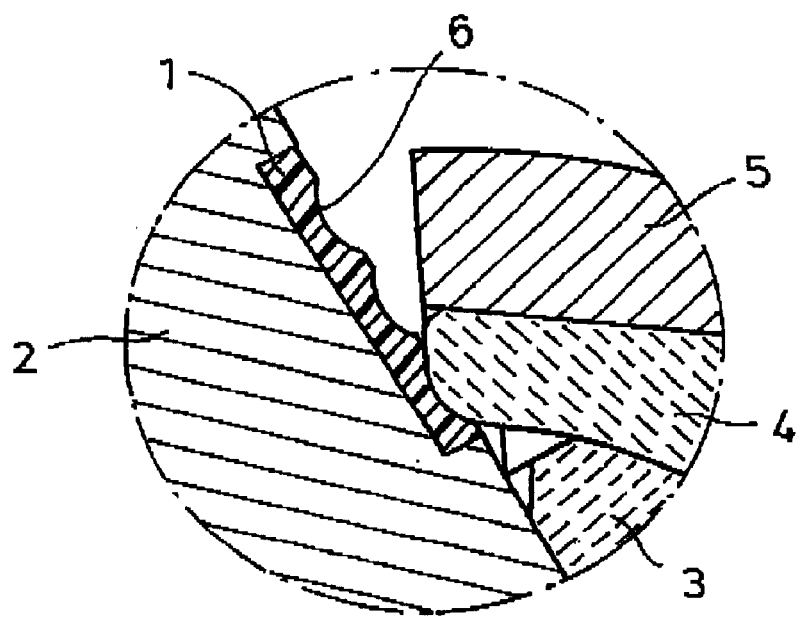
FIG. 2 is an enlarged view of the hip joint prosthesis shown in FIG. 1.
Figure 3:
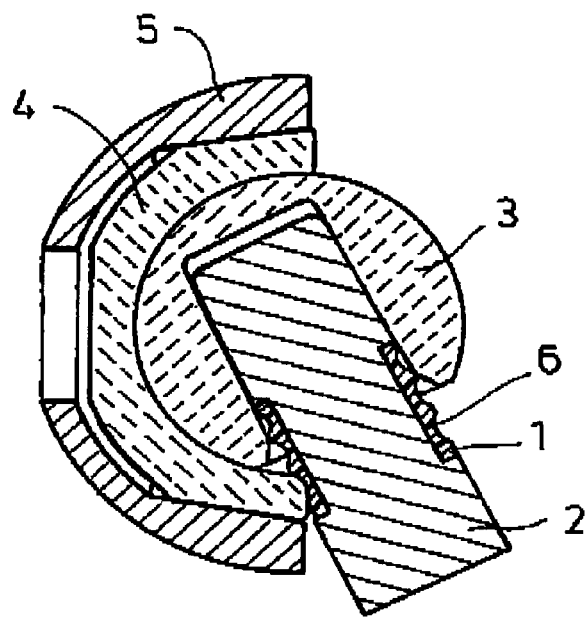
FIG. 3 is an embodiment of the invention with an elongated cushioning element.
Figure 4:
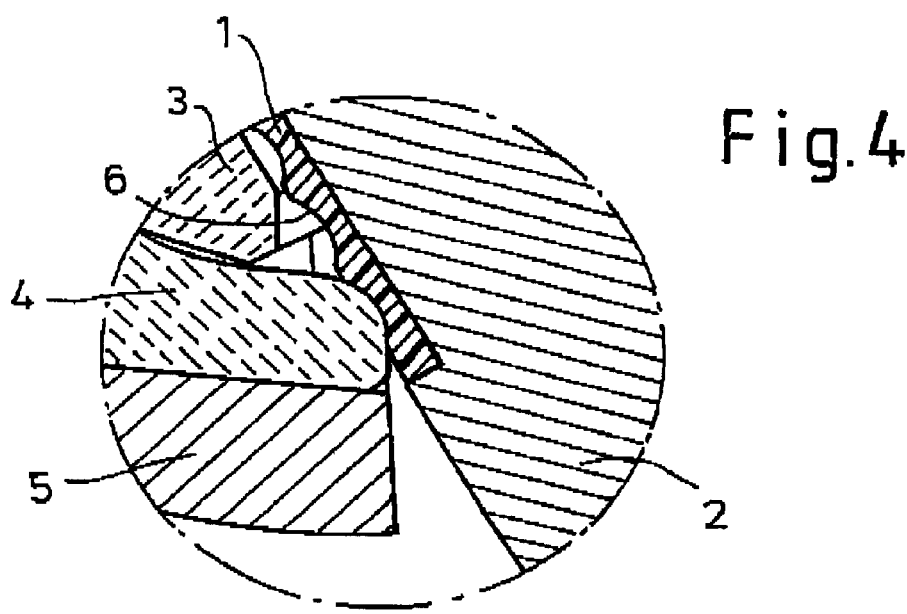
FIG. 4 is an enlarged view of the embodiment shown in FIG. 3.

FIGS. 3 and 4 show an embodiment similar to that of FIGS. 1 and 2, except that here the cushioning element 1 is elongated sufficiently to reach axially into the ball head 3 or the bore in ball head 3.

Figure 5:
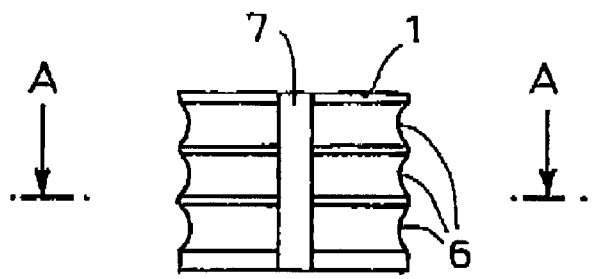
FIG. 5 is an elevational view of a cushioning element with an axial slot.
Figure 6:
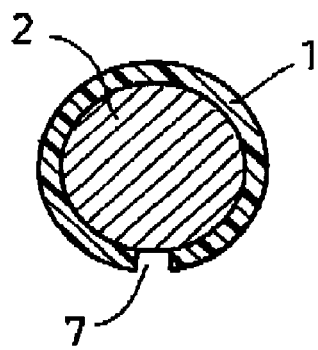
FIG. 6 is a section along A—A of FIG. 5 through the cushioning element surrounding the prosthesis shaft.

FIG. 5 is an elevational view of a cushioning element 1 with an axial slot 7 which serves to enable the cushioning element 1 to be mounted onto the prosthesis shaft 2. The cushioning element 1 is shaped as a ring and has circumferential indentations 6 on its exterior surface. FIG. 6 shows a section along line A—A of FIG. 5 through the cushioning element 1 surrounding the prosthesis shaft 2.

Figure 7:
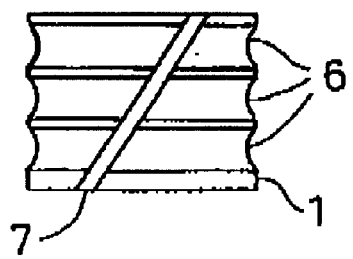
FIG. 7 is an elevational view of a cushioning element with a diagonal slot.
Figure 8:
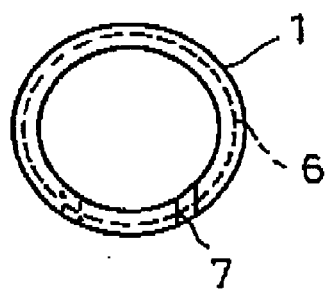
FIG. 8 is a plan view of the cushioning element shown in FIG. 7.

FIG. 7 shows in elevation a cushioning element 1 similar to the one shown in FIG. 5, but here the slot 7 runs diagonally. Circumferential indentations 6 are likewise present. FIG. 8 shows a plan view of the cushioning element of FIG. 7.

Figure 9:
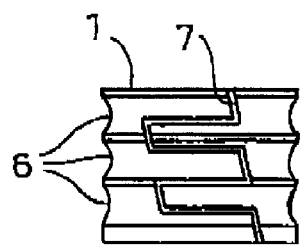
FIG. 9 is an elevational view of a cushioning element with a slot of saw-tooth-like shape.

FIG. 9 shows in elevation a cushioning element 1 with a slot 7 which is of saw-tooth-like shape. In all variant embodiments the ends of the slot 7 can overlap. The indentations 6 are the same as in the preceding figures.

Figure 10A:
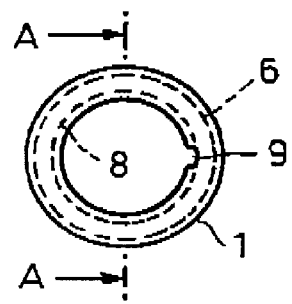
FIG. 10a shows cushioning element with cavities on the inside for containing body fluids.
Figure 10B:
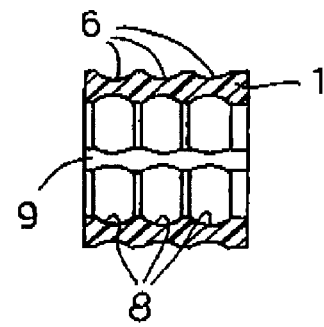

FIGS. 10a and 10b shows a damping element 1 with cavities 8 on the inside for containing body fluids. These cavities 5 are of undulating shape like the indentations 6 and are interconnected by a channel 9.

FIG. 10b shows a section along line A—A in FIG. 10a.

In case of an abutment of the prosthesis shaft 2 against the margin of the socket insert, these cavities 8 are compressed and the body fluid contained in them—substantially water, $H_2O$—is forced out. The result is the cushioning property of the cavities 8.

Figure 11:
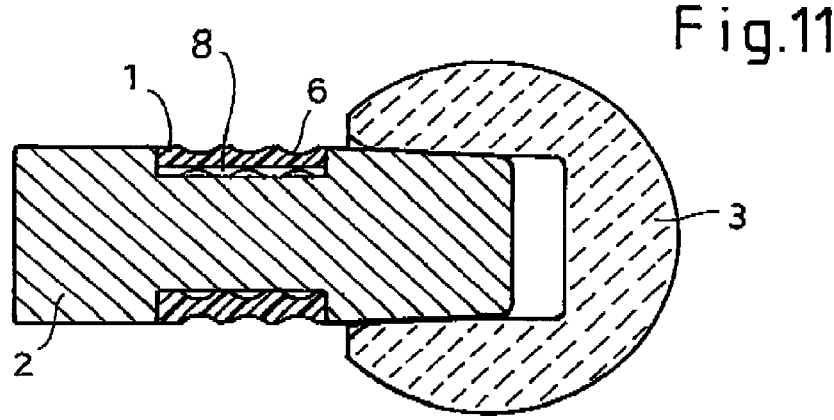
FIG. 11 shows a section through a prosthesis shaft with the installed ball head and the installed cushioning element with internal cavities.

FIG. 11 shows a section through a prosthesis shaft 2 with the installed ball head 3 and the installed cushioning element with internal cavities 8.

In the upper aspect of FIG. 11, elevations are provided on the prosthesis shaft 2, and the cushioning element 1 is thin, so that the cavities 8 are created.

In the bottom aspect of FIG. 11 an embodiment according to FIGS. 10a–b is illustrated, i.e., the cavities 8 are integrated into the cushioning element 1 by undulating depressions.

What is claimed is:

1. A hip joint prosthesis comprising an external metal shell;

a ball head;

a metal prosthesis shaft having a circumferential surface;

an internal socket insert in which said ball head can rotate, and a soft, biocompatible cushioning element;

wherein said ball head is joined to said metal prosthesis shaft of a femoral shaft and the movement of said metal prosthesis shaft is limited by abutting against a margin of the socket insert, wherein said soft, biocompatible cushioning element is applied to said circumferential surface of said metal prosthesis shaft in a region where said metal prosthesis shaft impacts said socket insert.

2. A hip joint prosthesis according to claim 1, wherein the cushioning element is a plastic.

3. A hip joint prosthesis according to claim 1, wherein the geometrical configuration of the cushioning element is adapted to the corresponding edge of the socket insert.

4. A hip joint prosthesis according to claim 1, wherein the geometrical configuration of the cushioning element is adapted to the corresponding edge of the socket insert.

5. A hip joint prosthesis according to claim 4, wherein socket insert indentations are provided on the outer surface of the cushioning element.

6. A hip joint prosthesis according to claim 1, wherein the cushioning element reaches in its axial length into the ball head.

7. A hip joint prosthesis according to claim 1, wherein the cushioning element is a ring.

8. A hip joint prosthesis according to claim 7, wherein a slot is arranged in the ring.

9. A hip joint prosthesis according to claim 8, wherein the ends of the slot are overlapping.

10. A hip joint prosthesis according to claim 7, wherein the slot is made axial, slanting and/or sawtooth-like.

11. A hip joint prosthesis according to claim 7, wherein the ends of the slot are overlapping.

12. A hip joint prosthesis according to claim 1, wherein between the cushioning element and the prosthesis shaft cavities are arranged to receive body fluids.

\* \* \* \* \*